US005695771A

United States Patent [19]
Boussouira et al.

[11] Patent Number: 5,695,771
[45] Date of Patent: Dec. 9, 1997

[54] COMPOSITION CONTAINING A NON-PHOTOCATALYTIC METAL OXIDE AND TOCOPHEROL ITS USE IN TREATING LIGHT INDUCED SIGNS OF AGING

[75] Inventors: Boudiaf Boussouira, Paris; Quang Lan Nguyen, Antony, both of France

[73] Assignee: L'Oreal, Paris, France

[21] Appl. No.: 548,680

[22] Filed: Oct. 26, 1995

Related U.S. Application Data

[62] Division of Ser. No. 402,655, Mar. 13, 1995, Pat. No. 5,589,179.

[30] Foreign Application Priority Data

Mar. 11, 1994 [FR] France ................................. 94-02882

[51] Int. Cl.⁶ ..................................................... A61K 7/48
[52] U.S. Cl. ........................... 424/401; 424/701; 514/458; 514/859; 514/886; 514/887; 514/944
[58] Field of Search ................................ 424/401, 701; 514/859, 458, 886, 887, 944

[56] References Cited

U.S. PATENT DOCUMENTS

| 5,114,716 | 5/1992 | Nguyen et al. | 424/401 |
| 5,445,823 | 8/1995 | Hall et al. | 424/401 |

FOREIGN PATENT DOCUMENTS

| A-535 446 | 4/1993 | European Pat. Off. |
| 92/01439 | 2/1992 | WIPO |
| 93/14773 | 8/1993 | WIPO |
| 84/02845 | 8/1994 | WIPO |

OTHER PUBLICATIONS

EP 579078 Abstract (Apr. 1994).
EP 0280606 Abstract (Aug. 1988).

*Primary Examiner*—Jyothsan Venkat
*Attorney, Agent, or Firm*—Oblon, Spivak, McClelland, Maier & Neustadt, P.C.

[57] ABSTRACT

Cosmetic and/or dermatological compositions containing a non-photocatalytic metal oxide and tocopherol and, optionally, a metal-inactivating complexing agent are effective for inhibiting the light-induced peroxidation of lipids, and in particular lipids of sebaceous origin such as squalene.

15 Claims, 1 Drawing Sheet

COMPOSITION CONTAINING A NON-PHOTOCATALYTIC METAL OXIDE AND TOCOPHEROL ITS USE IN TREATING LIGHT INDUCED SIGNS OF AGING

This is a division of application Ser. No. 08/402,655, filed on Mar. 13, 1995, now a U.S. Pat. No. 5,589,179.

BACKGROUND OF THE INVENTION

1. Field of the Invention

The present invention relates to compositions which contain a non-photocatalytic metal oxide and tocopherol, which are useful, in particular, in the cosmetics, pharmaceutical, veterinary and agri-foodstuffs fields. The present compositions make it possible, in particular, to inhibit the light-induced peroxidation of unsaturated lipids, and more especially lipids of sebaceous origin (sebum).

The compositions of the present invention may take the form of a cream which can be applied either to the face or to the scalp and hair, as well as to the human body. The present compositions can also serve as a base for a lipstick. More specifically, the present invention relates to compositions which contain a zinc oxide and tocopherol acting synergistically.

The present invention also relates to a method of combating and/or preventing skin irritations, skin inflammations, acne and immunosuppression, as well as to a method for combating and/or preventing the signs of aging. Such skin phenomena are, in particular, induced by solar radiation. The present invention further relates to a process for preserving products containing a photooxidizable lipid.

2. Discussion of the Background

The lipids occurring at the surface of the skin, scalp and hair are known to be continuously subjected to damaging external agents, in particular air, atmospheric pollutants and visible and most especially ultraviolet (UV) radiation.

These lipids are those which form part of the constituents of the skin or hair, as well as those which are secreted by the skin including the scalp, and/or those which are deposited on the skin or hair when products containing lipids are applied to the skin or hair.

The lipids most exposed to damaging external agents are those contained in the fatty secretions of the skin such as sebum, which is rich in squalene. The presence of six double bonds in squalene makes squalene sensitive to oxidation. Thus, on prolonged exposure to UV, squalene is photoperoxidized to give squalene peroxides.

This high production of squalene peroxides causes, in particular, a series of sequential degradations especially in and on the skin, giving rise to many skin disorders. Thus, these squalene peroxides participate in:

(i) the pathogenesis of ache, as described by Saint Léger et al (see *British Journal of Dermatology*, vol. 114, pp. 535–542 (1986) who point out that squalene peroxides are comedogenic;

(ii) premature skin aging, as described by Keiko OH Sawa et al (see *The Journal of Toxicology Sciences*, vol. 19, pp. 151–159 (1984)) who discuss the consequences of sun-induced skin burns;

(iii) irritation phenomena, as reported by Takayoshi Tanaka et al (see *J. Clin. Biochem. Nutr.*, vol. 1, pp. 201–207 (1986)) who draw attention to the damage caused, in particular, by the repeated use of some shampoos;

(iv) the production of malodorous volatile products (aldehydes, ketones, acids, and the like); and (v) immunosuppression of biochemical messengers of the biological effects of UV irradiation of the skin, as described by M. Picardo et al. (see *Photodermatol. Photoimmunol. Photomed.*, vol. 3, pp. 105–110 (1991)).

In order to limit the peroxidation of unsaturated lipids, it is known to apply to the skin photoprotective compositions containing at least one anti-free-radical agent and at least one screening agent.

This is the case, for example, with the complex composition described in FR-A 2666226 relating to a cream for combating photon intolerance, and which contains alpha-tocopherol among other anti-free-radical constituents and titanium oxide among several physical and chemical screening agents present in the composition. This composition has the drawback of affording little protection against ultraviolet radiation and of being unsuitable for the cosmetics and dermatological fields on account of problems associated with the "photocatalytic" activity of titanium oxide, as explained below.

In effect, the inventors have found, according to the headspace method, that titanium oxide, under ultraviolet exposure or after a few hours at 37° C., catalyses the production of peroxide radicals from the lipid constituents contained in cosmetic compositions. On application of these compositions to the skin, this gives rise to harmful effects such as inflammation. For a description of this method, reference may be made especially to the publications of Q. L. N'guyen et al, *Symposium of AFECG-SFC*, Bordeaux, May 1984, pp. 358–359, "Evaluation de l'oxydation aldéhydique dans les produits cosmétiques" ["Evaluation of aldehyde oxidation in cosmetic products"]; and of K. Warner et al, "Pentane formation and rancidity in vegetable oils", *Journal of Food Science*, vol. 39, pp. 761–765 (1974).

For this reason, in order to overcome the drawbacks associated with the use of titanium oxide, surface treatments of titanium oxide have been suggested, for example in WO-A-90/09777. However, such treatments do not enable the photocatalytic activity of titanium oxide to be decreased sufficiently, and use of the treated titanium can also cause skin damage on exposure to UV.

The beneficial properties of zinc oxide for the skin are, moreover, known. In particular, zinc oxide retains greases and moisture, absorbs UV, possesses good covering power and is, in addition, soothing (see, for example, the publication of L. D. Grady appearing in *The Journal of the Society of Cosmetic Chemistry:* 1947, July, volume 1). Thus, zinc oxide has been incorporated in cosmetic compositions such as face powders (see the above publication of L. D. Grady).

More recently, the company NIVEA has marketed a composition in mask form called "Masque 3 minutes Hydropurifiant", which contains, among other ingredients, zinc oxide for its astringent properties, tocopherol acetate for its activity in cell regeneration and kaolin to absorb the excess sebum. This composition is not designed to inhibit the photoperoxidation of lipids, and in particular squalene, and is not capable of inhibiting this photoperoxidation.

An anti-sun cream based on zinc oxide and about ten other constituents including an antioxidant is disclosed in GB-A-2,184,356. However, the use of a tocopherol as an antioxidant for the purpose of combating the photoperoxidation of unsaturated lipids, in particular those of sebaceous origin such as squalene is not taught.

Moreover, it is known from EP-A-579,078 to combine zinc oxide and tocopherol, but this document neither teaches nor suggests the inhibition of the photoperoxidation of unsaturated lipids by this combination, particularly since, in the examples, tocopherol is used in its acetate form, a form which is not capable of inhibiting this photoperoxidation.

Thus, the compositions known to date confer insufficient or even zero protection of the skin against the peroxidation of lipids of and on the skin.

Accordingly, there remains a need for compositions capable of inhibiting the active forms of oxygen, and in particular displaying effective activity in combating lipid peroxidation, in particular in combating squalene peroxidation, on exposure to ultraviolet light and/or to other oxidizing factors, and which is well tolerated by the skin and/or hair.

In the context of the present invention, the term "active forms of oxygen" is understood to mean forms of oxygen, free-radical or otherwise, such as, in particular, ROOH (R representing, in particular, the hydrocarbon chain of an unsaturated lipid), $OH^\cdot$, $ROO^\cdot$, $O_2H^\cdot$, $^1O_2$ and more especially ROOH where R is the hydrocarbon chain of squalene.

SUMMARY OF THE INVENTION

Accordingly, it is one object of the present invention to provide novel compositions useful for combating the peroxidation of unsaturated lipids.

It is another object of the present invention to provide novel compositions useful for combating the peroxidation of squalene.

It is another object of the present invention to provide novel compositions useful for combating the peroxidation of unsaturated lipids resulting from exposure to ultraviolet light and/or other oxidizing factors.

It is another objection of the present invention to provide novel compositions useful for combating the peroxidation of unsaturated lipids which are well tolerated by the skin and/or hair.

It is another object of the present invention to provide novel compositions useful for stabilizing compositions which contain an unsaturated lipid against peroxidation.

It is another object of the present invention to provide novel methods for combating the peroxidation of unsaturated lipids.

It is another object of the present invention to provide novel methods for combating the peroxidation of squalene.

It is another object of the present invention to provide novel methods for combating the peroxidation of unsaturated lipids resulting from exposure to ultraviolet light and/or other oxidizing factors.

It is another object of the present invention to provide novel methods for combating the peroxidation of unsaturated lipids which are well tolerated by the skin and/or hair.

It is another object of the present invention to provide novel methods for stabilizing compositions which contain an unsaturated lipid against peroxidation.

These and other objects, which will become apparent during the following detailed description, have been achieved by the inventors' discovery that compositions comprising at least one non-photocatalytic metal oxide and at least one tocopherol are effective for inhibiting the photoperoxidation of unsaturated lipids.

Thus, the inventors have found that the efficacy of such compositions depends on the choice of antioxidant to be combined with the non-photocatalytic metal oxide.

Accordingly, one embodiment of the present invention is a method for inhibiting the photoperoxidation of unsaturated lipids by applying a composition comprising at least one non-photocatalytic metal oxide and at least one tocopherol, in a cosmetic and/or dermatological composition.

A further embodiment of the present invention is a method for combating and/or preventing the light-induced signs of aging by applying to the skin a composition comprising at least one non-photocatalytic metal oxide and at least one tocopherol.

As a result of the fact that the compositions of the present invention instantaneously block the initiation of peroxidation reactions in the presence of radiation, the present compositions are especially useful for combating irritation or even inflammation of the skin, immunosuppression and acne which are induced by light.

Thus, a further embodiment of the present invention is a method for dermatological treatment for combating and/or preventing irritation, inflammation, immunosuppression and/or acne which are induced by the photoperoxidation, in particular, of squalene by applying the present composition to the skin.

According to a preferred embodiment of the present invention, the present composition further comprises at least one metal-inactivating complexing agent enabling the metals possibly present in the composition, and in particular those in the water used, to be complexed, and these metals hence to be rendered inactive.

Hence another embodiment of the present invention is a method for inhibiting the photoperoxidation of unsaturated lipids, by contacting the lipid with a composition which comprises at least one tocopherol, at least one non-photocatalytic metal oxide and at least one metal-inactivating complexing agent.

BRIEF DESCRIPTION OF THE DRAWING

A more complete appreciation of the invention and many of the attendant advantages thereof will be readily obtained as the same become better understood by reference to the following detailed description when considered in connection with the accompanying drawing, wherein.

DETAILED DESCRIPTION OF THE PREFERRED EMBODIMENTS

Figure 1:
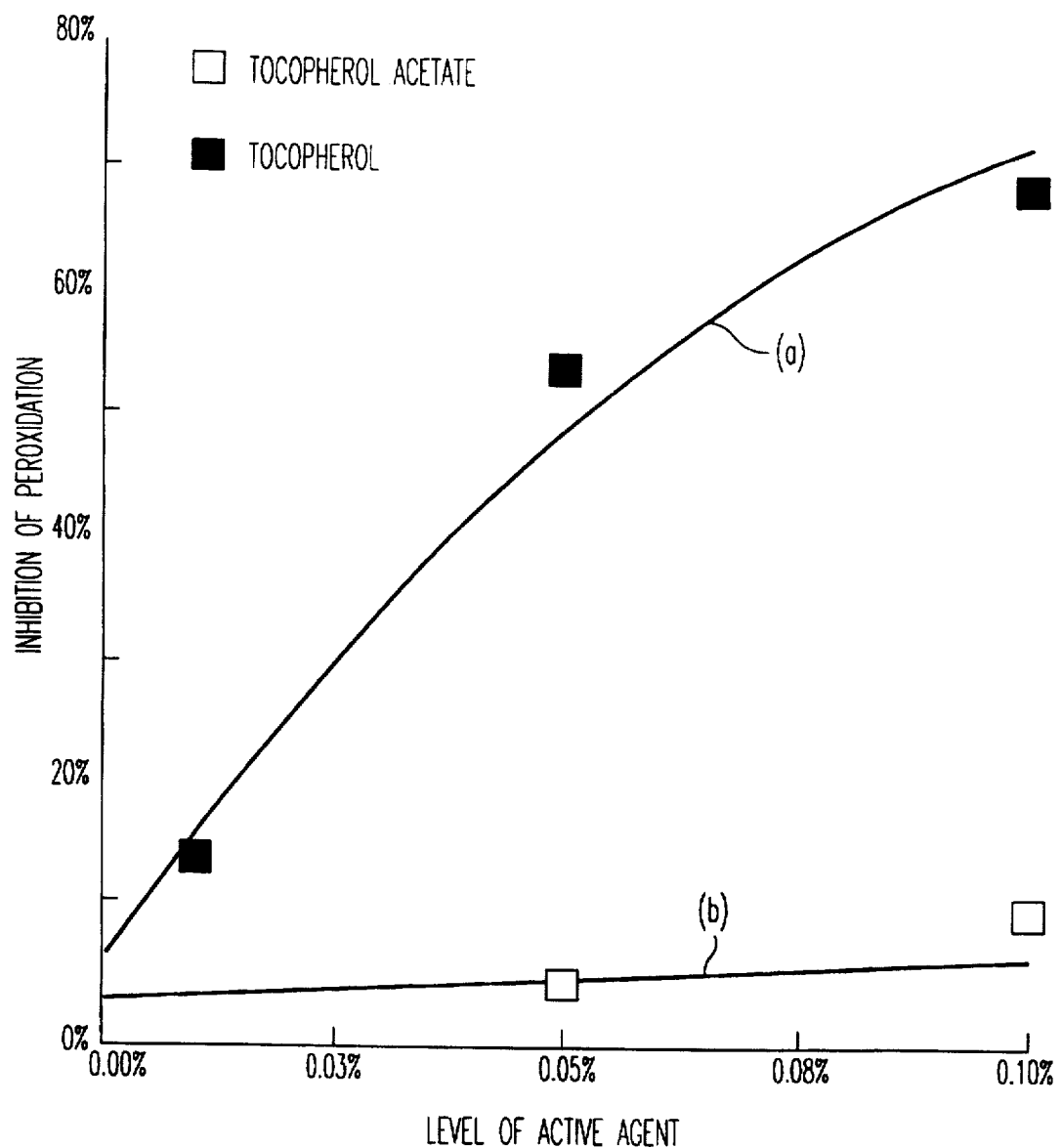
FIG. 1 is a graph comparing the efficacies of tocopherol and tocopherol acetate with respect to the peroxidation of sebum in an ex vivo test at an irridation of 5 Joules $UVA/cm^2$: □, tocopherol acetate; and ■, tocopherol.

In the context of the present invention, the term "tocopherol" is understood to mean α-tocopherol, β-tocopherol, γ-tocopherol and/or δ-tocopherol.

Furthermore, according to the present invention, one or more tocopherols and one or more metal oxides may be used.

The term "metal-inactivating complexing agent" is understood to mean an agent which prevents the formation of hydroxyl radicals, $OH^\cdot$, as a result of a strong uptake of the metals present in the composition, when these agents are subjected to radiation, in particular UV radiation. In particular, these agents effect the complexing under UV of the metals contained in water, and especially iron.

In particular, the inventors have observed that butylated hydroxytoluene (BHT) and superoxide dismutase (SOD), which are well-known antioxidants, have only a weak effect in combating lipid peroxidation, and cannot hence be usefully combined with a non-photocatalytic metal oxide in order to inhibit the peroxidation of unsaturated lipids.

According to the invention, the composition runs no risk of causing intolerance, and may be used with complete safety, in particular in the cosmetics, dermatological or even veterinary fields.

In addition, the present compositions provide effective protection against any oxidative attack without having recourse to other screening agents, in particular those of a chemical nature. Thus, the compositions of the present invention possess a more natural aspect, sought by the consumer, than the existing compositions in the cosmetics field, and are much simpler to produce than such compositions, and hence less expensive.

The compositions of the present invention can exist in various pharmaceutical dosage forms, and especially in the form of oil-in-water or water-in-oil emulsions, solutions, gels or vesicular dispersions. The present compositions can be a skincare cream, a shampoo, a lotion or a serum.

The non-photocatalytic metal oxide/tocopherol weight ratio in the composition of the present invention is typically from 100:1 to 1:4, and preferably from 10:1 to 2:1.

According to the invention, the non-photocatalytic metal oxide which is usable in the composition is preferably a bivalent metal oxide. This metal oxide may be coated or otherwise. As a non-photocatalytic bivalent metal oxide, zinc oxides, treated titanium oxides, selenium oxides, cerium oxides, magnesium oxides and zirconium oxides may be used. Preferably, zinc oxides are used.

Furthermore, the zinc oxide is present in the composition of the present invention preferably in the form of spherical particles. Advantageously, it should not contain traces of noxious heavy metals such as cadmium, lead, and the like. The average diameter of these nanoparticles is chosen, for example, to be from 1 nm to 500 nm, and preferably about 100 nm.

As zinc oxide, the one described in WO-A-92/13517 and marketed by the company Sunsmart under the name Z-cote may be used. This type of zinc oxide is transparent, which is an advantage in the cosmetics field from an aesthetic standpoint, the common pulverulent screening agents generally being opaque.

The metal oxide is generally present in the present composition in an amount of 0.1% to 5% by weight, preferably 0.5% to 2% by weight, based on the total weight of the composition.

According to the present invention, the tocopherol is present in the composition in the "free state", that is to say without any additional groups and in particular without an ester-forming group.

Preferably, the tocopherol used is a mixture of natural tocopherols, especially α-tocopherol, β-tocopherol, γ-tocopherol and δ-tocopherol; this mixture may be used, in particular, in an oil chosen from vegetable, mineral and silicone oils, and preferably vegetable oils.

As a mixture of natural tocopherols which is usable in the present invention, the one dissolved at a concentration of 50% in soya bean oil, sold by the company BIZEN under the name D *mixed tocopherola*, may be mentioned. The D-α-tocopherol sold by the company HENKEL under the name *Copherol* F1300 or alternatively those described in U.S. Pat. No. 4,144,325 may also be used.

The tocopherol (or mixture) may be present (active substance) in the composition of the present invention in an amount of 0.0005% to 10% by weight, preferably in an amount of at least 0.02% and up to 6% by weight, based on the total weight of the composition.

The metal-inactivating complexing agent which is usable in the composition of the present invention is, for example, a phosphonic acid derivative, and is chosen especially from 3-ethylenediaminetetra(methylenephosphonic acid), diethylenetriaminepenta(methylenephosphonic acid) and their sodium salts. Preferably, the complexing agent is diethylenetriaminepenta(methylenephosphonic acid) pentasodium salt.

As other complexing agents neutralizing the action of metals, diethylenetriaminepentaacetic acid, sold, for example, by the company SIGMA, may also be used.

Complexing agents such as ethylenediaminetetraacetic acid (EDTA), which is an iron chelator, possess a prooxidant effect under UV radiation, and hence cannot be used alone in the composition of the present invention designed to have an antioxidant effect. However, it is possible to use this type of agent in combination especially with a phosphonic acid derivative.

When the metal-inactivating complexing agent is present, it is present in an amount of from 0.005% to 0.5% by weight, preferably 0.005 to 0.3% by weight, based on the total weight of the composition.

Thus, a preferred composition according to the present invention for inhibiting the active forms of oxygen comprises, by weight, based on the total weight of the composition:

(a) from 0.05% to 2% of a mixture of natural tocopherols;
(b) from 0.5% to 5% of zinc oxide; and
(c) from 0.05% to 0.1% of diethylenetriaminepenta (methylenephosphonic acid) sodium salt.

The compositions of the present invention can, moreover, contain adjuvants, used alone or mixed, and especially those chosen from surfactants (emulsifier or coemulsifier) of the nonionic, anionic, cationic or amphoteric type, treatment agents, active agents, thickeners, suspending agents, colorants, perfumes, fillers, neutralizing agents, excipients (oils/water) and preservatives.

The adjuvants mentioned may be incorporated in the usual amounts commonly accepted, avoiding as far as possible adjuvants liable to release metals which catalyze oxidation. The adjuvants may be lipophilic or hydrophilic.

In the composition according to the present invention, the polymer based on polyacrylamide, $C_{13}$–$C_{14}$ isoparaffin and laureth-7 (according to the CTFA nomenclature) may advantageously be used as thickening agent.

The composition of the present invention is intended more especially for inhibiting the UV radiation-induced peroxidation of the unsaturated lipids of sebum, such as squalene.

Surprisingly, the inventors have discovered that the composition of the present invention very effectively inhibits the UV-induced formation of squalene peroxides as a result of a surprising synergistic effect between its two constituents, the non-photocatalytic metal oxide and tocopherol. This effect was demonstrated in ex vivo tests which are described in detail below.

In the particular case of the treatment of acne, a specific anti-acne, an antiseborrhoeic and/or an antibacterial agent, and especially piroctone olamine, sold under the name Octopirox by the company HOECHST, may also be advantageously incorporated in the composition of the present invention.

In another embodiment, the present invention provides a method for combating the signs of ageing which are induced by the photoperoxidation of squalene, by topical application of a composition according to the invention to the skin and/or scalp and/or hair.

By virtue of its beneficial properties, the composition of the present invention is suitable for the protection of any type of skin, and more especially greasy skins and so-called sensitive skins. It may also serve to protect the lips against chapping.

In the present method of combating the signs of ageing, the present composition is applied to the skin in an amount such that 0.002 to 0.1 mg/cm$^2$, preferably 0.01 to 0.04 mg/cm$^2$, of the non-photocatalytic metal oxide is applied to the skin, and 0.00001 to 0.2 mg/cm², preferably 0.0004 to 0.12 mg/cm², of the tocopherol is applied to the skin, and, if present in the composition, 0.0001 to 0.01 mg/cm², preferably 0.0001 to 0.006 mg/cm², of the metal-inactivating complexing agent is applied to the skin. The present composition may be applied one or more times daily or less frequently. In a preferred embodiment, the present composition is applied to the skin within one or two hours prior to exposure to intense radiation such as sunbathing.

On the same basis as the topical treatment, the composition of the invention may be used for preserving products containing a photooxidizable lipid. Thus, a further embodiment of the present invention is a process for preserving cosmetics, agri-foodstuffs and/or pharmaceutical products containing at least one photooxidizable lipid, which comprises incorporating a composition according to the present invention in the such products.

Other features of the present invention will become apparent in the course of the following descriptions of exemplary embodiments which are given for illustration of the invention and are not intended to be limiting thereof.

EXAMPLES

In the following examples and reference examples, the percentages are given by weight. The term "q.s. 100%" means that that ingredient is present in an amount sufficient to make the sum of amounts for all ingredients equal to 100%.

Example 1: Anti-acne cream for greasy skins

| Tocopherol and soya bean oil (50:50) | 0.5% |
|---|---|
| Glyceryl stearate | 0.3% |
| FD and C Red NO.4 (colorant) | 0.0001% |
| Acid Yellow 3 (colorant) | 0.0005% |
| Methyl para-hydroxybenzoate (preservative) | 2% |
| Hexamidine diisethionate (preservative) | 0.03% |
| Piroctone olamine (anti-acne) | 0.2% |
| Perfume | 0.3% |
| Triethanolamine (neutralizing agent) | 0.002% |
| Ethylenediaminetetra(methylenephosphonic acid) pentasodium salt | 0.01% |
| Zinc oxide | 2% |
| Xanthan gum (thickener) | 0.3% |
| Polyacrylamide/$C_{13}$-$C_{14}$ isoparaffin/laureth-7 (thickener) | 2% |
| Cyclomethicone (oil) | 6% |
| Glycerol (active agent) | 3% |
| Propylene glycol (active agent) | 6% |
| Cetyl alcohol (coemulsifier) | 1.0% |
| PEG-20 stearate (emulsifier) | 1.7% |
| D-Panthenol (active agent) | 1% |
| Water q.s. | 100% |

The cream thus prepared has a pH value of 6 to 7 and protects the skin, and especially the lipid constituents at the surface of the skin, against the adverse effects of UV. It may be applied every morning.

Reference Example 1

A cream is prepared having the same composition as that of Example 1 except for the zinc oxide.

Reference Example 2

A cream is prepared having the same composition as that of Example 1 except for the tocopherol.

Reference Example 3

A cream is prepared having the same composition as that of Example 1 except for the zinc oxide and the tocopherol (placebo).

To measure the respective efficacy of the composition of the invention (Ex. 1), as well as that of the compositions of the above reference examples, an ex vivo test is performed according to the following protocol:

A sebum sample is taken from the forehead of volunteers using four 17.4 cm² hydrophilic filter papers. The composition according to Example 1 is then applied to one of these four filter papers in the proportion of 4 mg/cm². Approximately 4 mg/cm² of the compositions of Reference Example 1, of Reference Example 2, and of the placebo (without zinc oxide or tocopherol) are then applied to the second, third, and fourth filters, respectively. The samples were all subjected to a dose of UVA of 5 joules per cm² for 50 min. The UV source used has a power of 2 mw/cm².

The results obtained are recorded in Table I, which shows the values for percentage inhibition of photoperoxidation obtained for Example 1 and the Reference Examples, respectively.

TABLE I

| Ex. 1 (Invention) | Reference Ex. 1 | Reference EX. 2 | Reference Ex. 3 |
|---|---|---|---|
| 65% | 9% | 18% | 0% |

Hence it is seen from Table I that the level of inhibition achieved with the composition of the present invention (65%) is markedly higher than the sum of the levels of inhibition (9%+18%) obtained using tocopherol and zinc oxide taken separately. It follows that tocopherol unexpectedly increases the efficacy of zinc oxide, and vice versa.

Example 2: Non-irritant shampoo

| Zinc oxide | 0.5% |
|---|---|
| Carbomer (*) | 0.2% |
| Triethanolamine (neutralizing agent) | 0.2% |
| MEA-laureth sulfate (**) (active substance) | 10% |
| Coco-betaine (**) | 2% |
| Cocoamide DEA (**) | 3% |
| Tocopherol and soya bean oil (50:50) | 0.2% |
| Perfume | q.s. |
| Water q.s. | 100% |

(*) Carbopol 980 sold by the company Goodrich
(**) According to the CTFA nomenclature Example 3: Protective gel for sensitive skins

| Tocopherol and soya bean oil | 0.5% |
|---|---|
| FD and C Red NO. 4 | 0.0001% |
| Acid Yellow 3 | 0.0005% |
| Methyl para-hydroxybenzoate | 0.18% |
| Hexamidine diisethionate | 0.03% |
| Perfume | 0.3% |
| Triethanolamine | 0.002% |
| Ethylenediaminetetra (methylenephosphonic acid) pentasodium salt | 0.01% |
| Zinc oxide | 2% |
| Xanthan gum | 0.3% |
| Polyacrylamide/$C_{13}$-$C_{14}$ isoparaffin/laureth-7 | 2% |
| Cyclomethicone | 6% |
| Glycerol | 3% |
| Propylene glycol | 6% |
| D-Panthenol | 1% |
| Water q.s. | 100% |

Ex Vivo Comparison

An ex vivo test is presented below showing the need to use a free tocopherol and not a tocopherol derivative such as tocopherol acetate. FIG. 1 shows the curves for inhibition of the peroxidation of sebum.

The ordinate axis corresponds to the percentage inhibition of peroxidation, and the abscissa axis corresponds to the tocopherol or tocopherol acetate concentration. The curve (a) corresponds to tocopherol and the curve (b) to tocopherol acetate. On comparing these two curves, it is clearly apparent that only tocopherol enables a good inhibition of the peroxidation of sebum to be obtained.

The test protocol was as follows:

for each curve (a) and (b), a sebum sample was taken from the forehead of an individual using two hydrophilic filters; in each case, a placebo was applied to one filter and the cream containing the active agent to the other filter, that is to say tocopherol in one case and tocopherol acetate in the other case, the active agent being present in the cream at a specified concentration, and the placebo and the cream being applied at a concentration of 3 mg/cm$^2$;

the filters were then subjected to an irradiation of 5 joules UVA per cm$^2$;

the level of squalene peroxides on the filters was then determined by reverse-phase chromatography and chemi-luminescence;

the results obtained are shown in FIG. 1.

The creams and the placebo have the compositions shown in Table II

TABLE II

| Composition | Placebo | Cream containing 0.05% | Cream containing 0.1% |
|---|---|---|---|
| Oily phase | 35% | 34.95% | 34.9% |
| Active agent | 0% | 0.05% | 0.1% |
| Water | 65% | 65% | 65% |

The oily phase has the following percentage composition:

| | |
|---|---|
| Cetyl alcohol | 14% |
| Glyceryl stearate | 9% |
| PEG-50 stearate | 9% |
| Caprylic/capric triglycerides | 9% |
| Mineral oil q.s. | 100% |

This application is based on French Patent Application No. 94-02882, filed on Mar. 11, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for treating the light-induced signs of aging, comprising applying to skin a composition which comprises at least one non-photocatalytic metal oxide, a metal-inactivating complexing agent, and at least one tocopherol.

2. The method of claim 1, wherein said metal-inactivating complexing agent is present in said composition in an amount of 0.005% to 0.1% by weight, based on the total weight of the composition.

3. The method of claim 1, wherein said metal-inactivating complexing agent is a phosphonic acid derivative.

4. The method of claim 3, wherein said phosphonic acid derivative is selected from the group consisting of ethylenediaminetetra(methylenephosphonic acid), diethylenetriaminepenta(methylenephosphonic acid), and sodium salts thereof.

5. The method of claim 1, wherein said non-photcatalytic metal oxide and said tocopherol are present in a weight ratio of from 100:1 to 1:4.

6. The method of claim 5, wherein said weight ratio is from 10:1 to 2:1.

7. The method of claim 1, wherein said non-photocatalytic metal oxide is a bivalent metal oxide.

8. The method of claim 7, wherein said bivalent metal oxide is zinc oxide.

9. The method of claim 8, wherein said zinc oxide is in the form of spherical particles with an average diameter of from 1 nm to 500 nm.

10. The method of claim 1, wherein said tocopherol is present in an amount of at least 0.02% to 6% by weight, based on the total weight of said composition.

11. The method of claim 1, wherein said tocopherol is a mixture of natural tocopherols.

12. The method of claim 1, wherein said composition further comprises an adjuvant selected from the group consisting of nonionic surfactants, anionic surfactants, cationic surfactants, amphoteric surfactants, treatment agents, active agents, thickeners, suspending agents, colorants, perfumes, fillers, neutralizing agents, excipients, preservatives, and mixtures thereof.

13. The method of claim 12, wherein said adjuvant is an anti-acne agent.

14. The method of claim 1, wherein said composition is a cream having a pH value of 6–7, and further comprises a polymer based on polyacrylamide, $C_{13}$–$C_{14}$ isoparaffin and laureth-7.

15. The method of claim 1, wherein said tocopherol is selected from the group consisting of α-tocopherol, β-tocopherol, γ-tocopherol, δ-tocopherol and a mixture thereof.

* * * * *